US00PP24206P2

(12) United States Plant Patent
van der Knaap

(10) Patent No.: US PP24,206 P2
(45) Date of Patent: Jan. 28, 2014

(54) ***CURCUMA* PLANT NAMED 'CURCHOCWI'**

(50) Latin Name: *Curcuma hybrida*
Varietal Denomination: Curchocwi

(75) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 120 days.

(21) Appl. No.: 13/385,164

(22) Filed: Feb. 6, 2012

(51) Int. Cl.
*A01H 5/00* (2006.01)

(52) U.S. Cl.
USPC ..... Plt./421

(58) Field of Classification Search
USPC ..... Plt./421
See application file for complete search history.

*Primary Examiner* — June Hwu
(74) *Attorney, Agent, or Firm* — C. A. Whealy

(57) ABSTRACT

A new and distinct cultivar of *Curcuma* plant named 'Curchocwi', characterized by its upright and columnar plant habit with outwardly arching leaves; freely clumping growth habit; large relatively broad leaves; freely flowering habit; and flowers with white-colored flower bracts that are positioned above the foliar plane on strong and erect peduncles.

2 Drawing Sheets

Botanical designation: *Curcuma hybrida.*
Cultivar denomination: 'Curchocwi'.

BACKGROUND OF THE INVENTION

The present invention relates to a new and distinct cultivar of *Curcuma* plant, botanically known as *Curcuma hybrida* and hereinafter referred to by the name 'Curchocwi'.

The new *Curcuma* plant is a product of a controlled breeding program conducted by the Inventor in Naaldwijk, The Netherlands. The objective of the breeding program is to create new *Curcumas* that have uniform plant habit, good container performance and attractive inflorescence coloration.

The new *Curcuma* plant originated from a cross-pollination made by the Inventor in May, 2007 in Naaldwijk, The Netherlands of a proprietary selection of *Curcuma hybrida* identified as code number 20041120-001, not patented, as the female, or seed, parent with a proprietary selection of *Curcuma hybrida* identified as code number 20051012-003, not patented, as the male, or pollen, parent. The new *Curcuma* plant was discovered and selected by the Inventor as a single flowering plant within the progeny of the stated cross-pollination in a controlled greenhouse environment in Naaldwijk, The Netherlands on Aug. 13, 2008.

Asexual reproduction of the new *Curcuma* plant by tissue culture in a controlled environment in Maasdijk, The Netherlands since September, 2008 has shown that the unique features of this new *Curcuma* plant are stable and reproduced true to type in successive generations of asexual reproduction.

SUMMARY OF THE INVENTION

Plants of the new *Curcuma* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curchocwi'.

These characteristics in combination distinguish 'Curchocwi' as a new and distinct *Curcuma* plant:

1. Upright and columnar plant habit with outwardly arching leaves.
2. Freely clumping growth habit.
3. Large relatively broad leaves.
4. Freely flowering habit.
5. Flowers with white-colored flower bracts that are positioned above the foliar plane on strong and erect peduncles.

Plants of the new *Curcuma* differ from plants of the female parent selection in the following characteristics:

1. Plants of the new *Curcuma* and the female parent selection differ in leaf color as plants of the female parent selection have leaves with red-colored venation.
2. Plants of the new *Curcuma* and the female parent selection differ in flower bract color as plants of the female parent selection have pink-colored flower bracts.

Plants of the new *Curcuma* differ from plants of the male parent selection in the following characteristics:

1. Plants of the new *Curcuma* have narrower leaves than plants of the male parent selection.
2. Plants of the new *Curcuma* and the male parent selection differ in flower bract color as plants of the male parent selection have light pink-colored flower bracts.

Plants of the new *Curcuma* can also be compared to plants of *Curcuma hybrida* 'Curzena', disclosed in U.S. Plant Pat. No. 19,956. In side-by-side comparisons conducted in Naaldwijk, The Netherlands, plants of the new *Curcuma* differed from plants of 'Curzena' in the following characteristics:

1. Plants of the new *Curcuma* were more freely clumping than plants of 'Curzena'.
2. Plants of the new *Curcuma* had broader leaves than plants of 'Curzena'.
3. Plants of the new *Curcuma* and 'Curzena' differed in leaf color as plants of 'Curzena' had leaves with red-colored venation.
4. Plants of the new *Curcuma* and 'Curzena' differed in flower bract color as plants of 'Curzena' had pink-colored flower bracts.

BRIEF DESCRIPTION OF THE PHOTOGRAPHS

The accompanying photographs illustrate the overall appearance of the new *Curcuma* showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curchocwi' grown in a container.

The photograph on the second sheet is a close-up view of a typical inflorescence of 'Curchocwi'.

DETAILED BOTANICAL DESCRIPTION

The aforementioned photographs and following observations and measurements describe plants grown during the late autumn in 17-cm containers in a glass-covered greenhouse in Naaldwijk, The Netherlands and under environmental conditions and cultural practices which approximate those generally used in commercial *Curcuma* production. During the production of the plants, day temperatures ranged from 19° C. to 28° C., night temperatures ranged from 19° C. to 22° C. and light levels averaged 55,000 lux. Plants were 18 weeks old when the photographs and the detailed description were taken. In the following description, color references are made to The Royal Horticultural Society Colour Chart, 2007 Edition, except where general terms of ordinary dictionary significance are used.

Botanical classification: *Curcuma hybrida* 'Curchocwi'.

Parentage:

*Female, or seed, parent*.—Proprietary selection of *Curcuma hybrida* identified as code number 20041120-001, not patented.

*Male, or pollen, parent*.—Proprietary selection of *Curcuma hybrida* identified as code number 20051012-003, not patented.

Propagation:

*Type*.—By tissue culture.

*Time to initiate roots*.—About ten days at 23° C.

*Time to produce a rooted young plant*.—About 28 to 30 days at 21° C.

*Root description*.—Medium in thickness, slightly fleshy; close to 155D in color.

*Rooting habit*.—Moderately branching, medium density.

*Number of rhizomes produced per plant*.—About seven.

*Rhizome diameter*.—About 9 mm.

Plant description:

*Growth habit*.—Upright and columnar with outwardly arching leaves; freely clumping habit.

*Plant height (soil level to top of inflorescences)*.—About 51.5 cm.

*Plant diameter*.—About 45 cm.

Foliage description:

*Leaf arrangement*.—Alternate; simple.

*Length, fully expanded*.—About 47.4 cm.

*Width, fully expanded*.—About 9.5 cm.

*Shape*.—Lanceolate to narrowly elliptic.

*Apex*.—Elongated apiculate.

*Base*.—Sheathing; wings, about 9.8 cm in length.

*Margin*.—Entire.

*Venation*.—Parallel.

*Aspect*.—Initially upright, then outwardly arching.

*Texture*.—Smooth, glabrous.

*Color*.—Developing and fully expanded leaves, upper surface: Close to N137C; venation, close to N137A. Developing and fully expanded leaves, lower surface: Between 147B and 191A; venation, close to N137B.

Inflorescence description:

*Arrangement*.—Dense terminal spike inflorescences develop directly from the rhizome with numerous bracts and bracteole flowers in bract axils.

*Time to flower*.—In The Netherlands, plants flower from spring into autumn; flowering continuous during this period.

*Flower longevity*.—Flowers last about three days on the plant; flowers not persistent.

*Fragrance*.—None detected.

*Inflorescence length*.—About 14 cm.

*Inflorescence diameter*.—About 8.8 cm.

*Flowers*.—Length: About 2.4 cm. Diameter: About 1.1 cm. Shape: Zygomorphic with three petals; lower petal (labellum) is conspicuous; calyx with three sepals. Color: Upper two petals and sepals, upper surface: Close to 83A to 83B. Upper two petals and sepals, lower surface: Close to 83C to 83D. Lower petal (labellum), upper surface: Close to 85A; towards the apex, close to N87A to N87B. Lower petal (labellum), lower surface: Close to 85A; towards the apex, close to N87B.

*Flower bracts*.—Quantity: About 15 per inflorescence. Length, upper bracts: About 6.5 cm. Width, upper bracts: About 3.6 cm. Length, lower bracts: About 3.3 cm. Width, upper bracts: About 3.6 cm. Shape, upper bracts: Ovate; apex, obtuse; base, cuneate; margins, entire. Shape, lower bracts: Orbicular; apex, obtuse; base, cuneate; margins, entire. Texture, upper and lower surfaces: Smooth, glabrous. Color: Upper bracts, upper surface: Close to NN155D; towards the apex and base, close to 145A to 145D. Upper bracts, lower surface: Close to NN155D; towards the apex, close to 144D; towards the base, close to 145B. Lower bracts, upper surface: Close to 146D; towards the apex, close to 144A. Upper bracts, lower surface: Close to 144B; distally, strongly tinged with close to 175A to 175B.

*Peduncle*.—Length: About 38.1 cm. Diameter: About 6 mm. Texture: Smooth, glabrous. Angle: Upright, erect. Color: Between 143A and 144A.

*Stamens*.—Quantity: Two per flower. Filament: Length: About 1.4 cm. Diameter: About 3 mm. Color: Close to 155B; towards the apex, tinged with close to 85A. Anther color: Close to 155B tinged with close to 84A. Pollen amount: None observed.

*Pistils*.—Quantity per flower: One. Pistil length: About 1.8 cm. Stigma: Length: About 2 mm. Diameter: About 1.5 mm. Color: Close to N155A. Style: Length: About 1.7 cm. Diameter: About 0.5 mm. Color: Close to N155A.

*Seeds and fruits*.—Seed and fruit development have not been observed on plants of the new *Curcuma*.

Disease & pest resistance: Plants of the new *Curcuma* have not been observed to be resistant to pathogens or pests common to *Curcuma*.

Temperature tolerance: Plants of the new *Curcuma* have been observed to be tolerant to temperatures ranging from about 16° C. to about 30° C.

It is claimed:

1. A new and distinct *Curcuma* plant named 'Curchocwi' as illustrated and described.

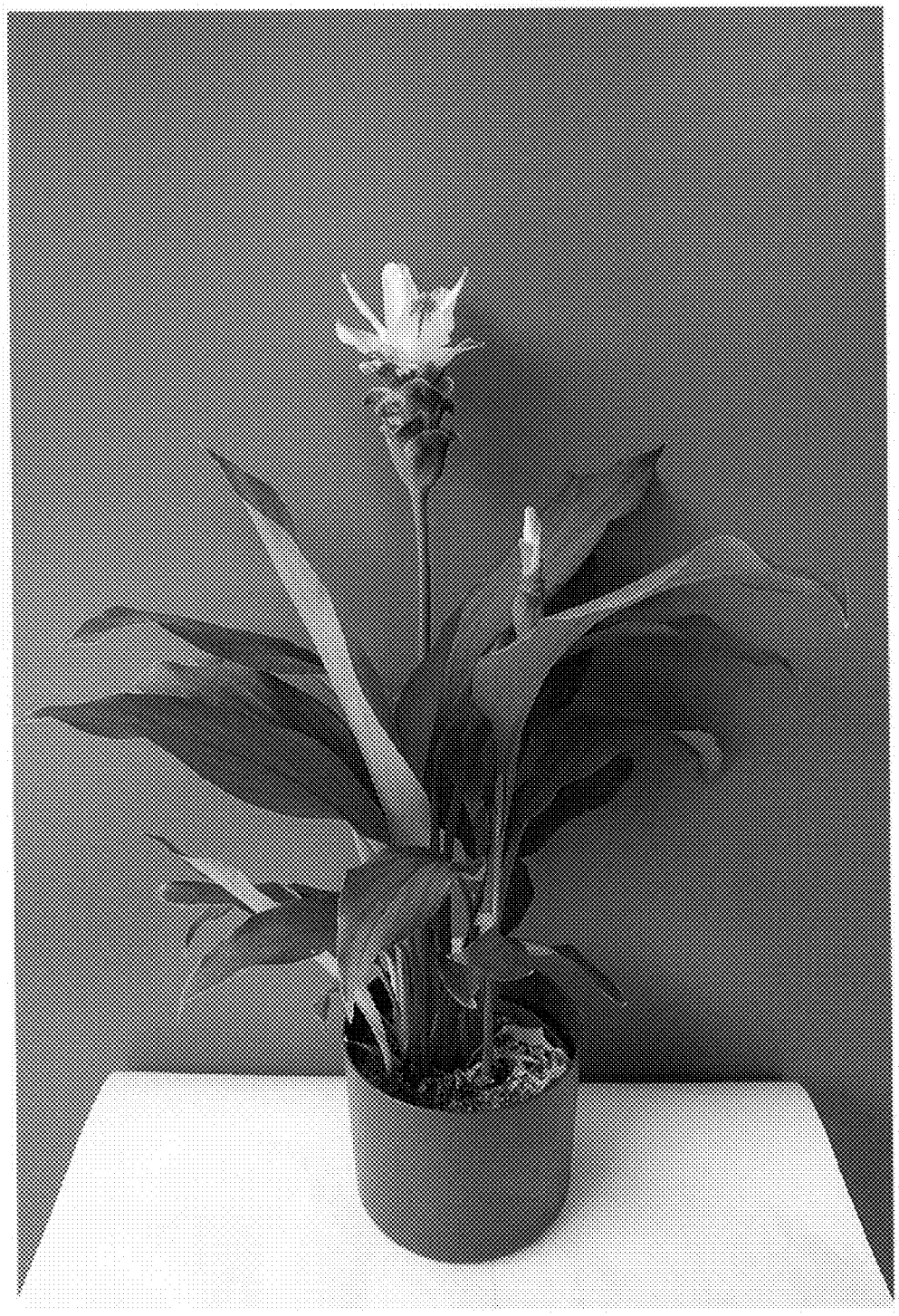

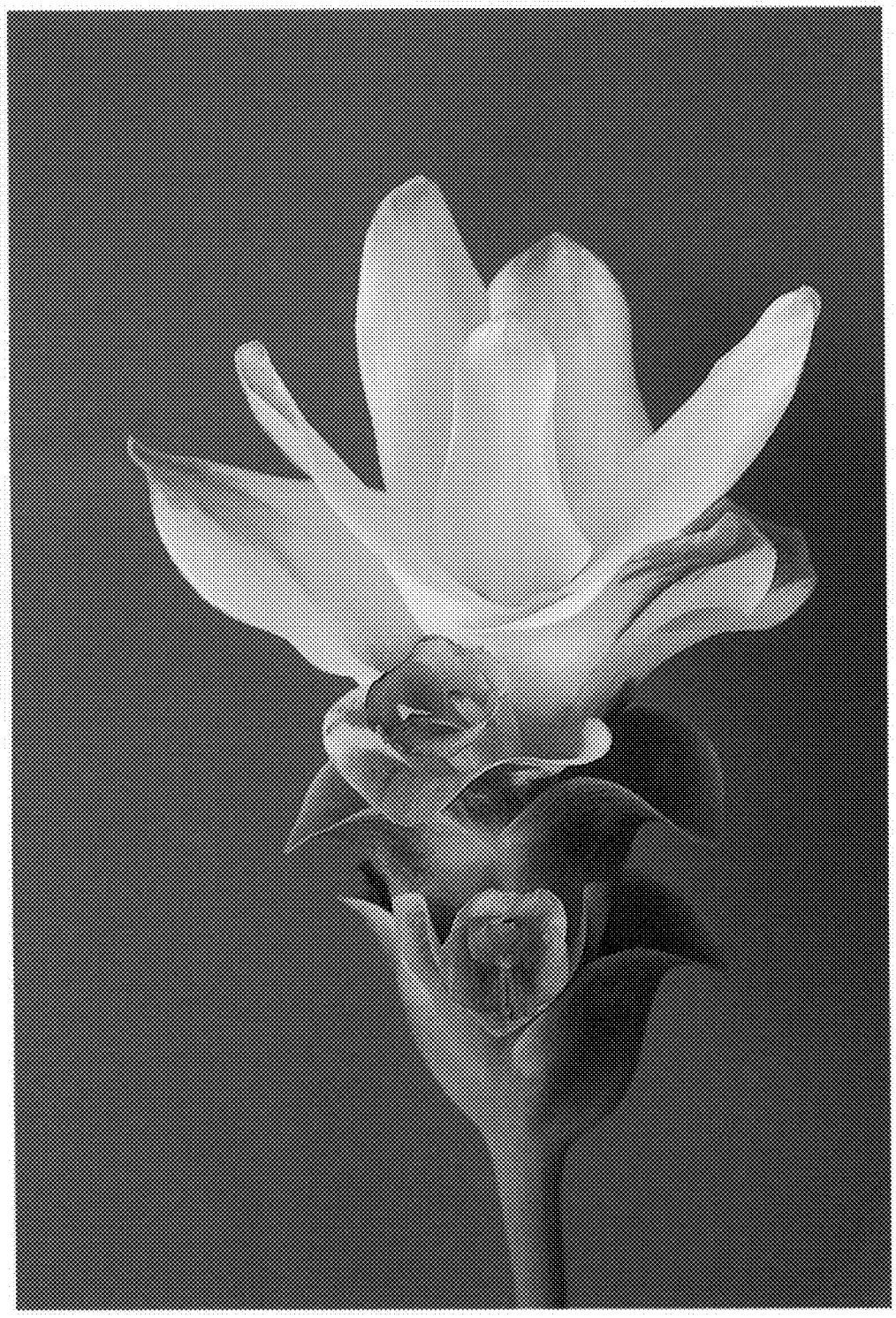

* * * * *